(12) United States Patent
Tal

(10) Patent No.: US 7,862,575 B2
(45) Date of Patent: Jan. 4, 2011

(54) VASCULAR ABLATION APPARATUS AND METHOD

(75) Inventor: Michael G. Tal, Woodbridge, CT (US)

(73) Assignee: Yale University, New Haven, CT (US)

( * ) Notice: Subject to any disclaimer, the term of this patent is extended or adjusted under 35 U.S.C. 154(b) by 1329 days.

(21) Appl. No.: 10/736,535

(22) Filed: Dec. 17, 2003

(65) Prior Publication Data

US 2005/0055040 A1    Mar. 10, 2005

Related U.S. Application Data

(60) Provisional application No. 60/501,423, filed on Sep. 10, 2003.

(51) Int. Cl.
*A61B 17/22* (2006.01)

(52) U.S. Cl. ...................... 606/159; 128/898

(58) Field of Classification Search .............. 604/96.01, 604/508, 101.1, 509; 606/159, 192, 194, 606/170, 139, 153; 128/898
See application file for complete search history.

(56) References Cited

U.S. PATENT DOCUMENTS

| 4,728,319 | A |   | 3/1988  | Masch       |         |
|-----------|---|---|---------|-------------|---------|
| 5,022,399 | A | * | 6/1991  | Biegeleisen | 600/468 |
| 5,047,013 | A |   | 9/1991  | Rossdeutscher |       |
| 5,074,871 | A |   | 12/1991 | Groshong    |         |
| 5,087,244 | A |   | 2/1992  | Wolinsky et al. |     |
| 5,370,653 | A | * | 12/1994 | Cragg       | 606/170 |
| 5,415,636 | A | * | 5/1995  | Forman      | 604/101.03 |
| 5,628,730 | A |   | 5/1997  | Shapland et al. |     |
| 5,709,657 | A |   | 1/1998  | Zimmon      |         |
| 5,766,191 | A |   | 6/1998  | Trerotola   |         |

(Continued)

FOREIGN PATENT DOCUMENTS

CA    2405273    4/2001

(Continued)

OTHER PUBLICATIONS

Slerosant treatment of varicose veins and deep vein thrombosis, vol. 119 No. 11, Nov. 1984.*

(Continued)

*Primary Examiner*—Gary Jackson
*Assistant Examiner*—Victor X Nguyen
(74) *Attorney, Agent, or Firm*—Welsh Flaxman & Gitler LLC

(57) ABSTRACT

An apparatus for the treatment of venous stasis includes an elongated intraluminal member shaped and dimensioned for passage through vessels of a subject. The intraluminal member includes a proximal end and a distal end. A conduit extends from proximate the proximal end of the intraluminal member to proximate the distal end of the intraluminal member. The conduit is shaped and dimensioned for fluid communication between the proximal end of the intraluminal member and the distal end of the intraluminal member. The distal end of the intraluminal member includes disruption means proximate thereto for ablating a predetermined vessel wall. A method is also provided for the treatment of venous stasis. The method is achieved by advancing an elongated intraluminal member through a vein to a treatment site, activating the intraluminal member for ablation of the treatment site and injecting sclerosant into the vein at the treatment site.

16 Claims, 5 Drawing Sheets

U.S. PATENT DOCUMENTS

| | | | |
|---|---|---|---|
| 5,836,905 A * | 11/1998 | Lemelson et al. | 604/21 |
| 5,882,329 A | 3/1999 | Patterson et al. | |
| 5,902,266 A | 5/1999 | Leone et al. | |
| 6,048,332 A * | 4/2000 | Duffy et al. | 604/103.08 |
| 6,090,118 A | 7/2000 | McGuckin, Jr. | |
| 6,159,196 A * | 12/2000 | Ruiz | 604/500 |
| 6,231,518 B1 | 5/2001 | Grabek et al. | |
| D450,843 S | 11/2001 | McGuckin, Jr. et al. | |
| 6,369,039 B1 | 4/2002 | Palasis et al. | |
| 6,484,727 B1 | 11/2002 | Vaska et al. | |
| 6,544,221 B1 | 4/2003 | Kokish et al. | |
| 6,602,264 B1 | 8/2003 | McGuckin, Jr. | |
| 6,733,473 B1 | 5/2004 | Reifart et al. | |
| 6,824,551 B2 | 11/2004 | Trerotola | |
| 7,083,643 B2 * | 8/2006 | Whalen et al. | 623/1.42 |
| 7,108,704 B2 | 9/2006 | Trerotola | |
| 7,211,073 B2 | 5/2007 | Fitzgerald et al. | |
| 7,285,126 B2 | 10/2007 | Sepetka et al. | |
| 2002/0010418 A1 | 1/2002 | Lary et al. | |
| 2002/0077594 A1 | 6/2002 | Chien et al. | |
| 2002/0188276 A1 * | 12/2002 | Evans et al. | 604/509 |
| 2003/0004568 A1 * | 1/2003 | Ken et al. | 623/1.46 |
| 2003/0045860 A1 | 3/2003 | Leu | |
| 2003/0120256 A1 | 6/2003 | Lary et al. | |

FOREIGN PATENT DOCUMENTS

| | | |
|---|---|---|
| DE | 10059742 A1 | 6/2002 |
| EP | 0501081 | 9/1992 |
| FR | 2651682 | 3/1991 |

OTHER PUBLICATIONS

PCT/US04/15858, Patent Cooperation Treaty PCT International Search Report, Form PCT/ISA/210, pp. 1-2.

PCT/US04/15858, Patent Cooperation Treaty PCT Written Opinion of the International Searching Authority, Form PCT/ISA/237, pp. 1-3.

* cited by examiner

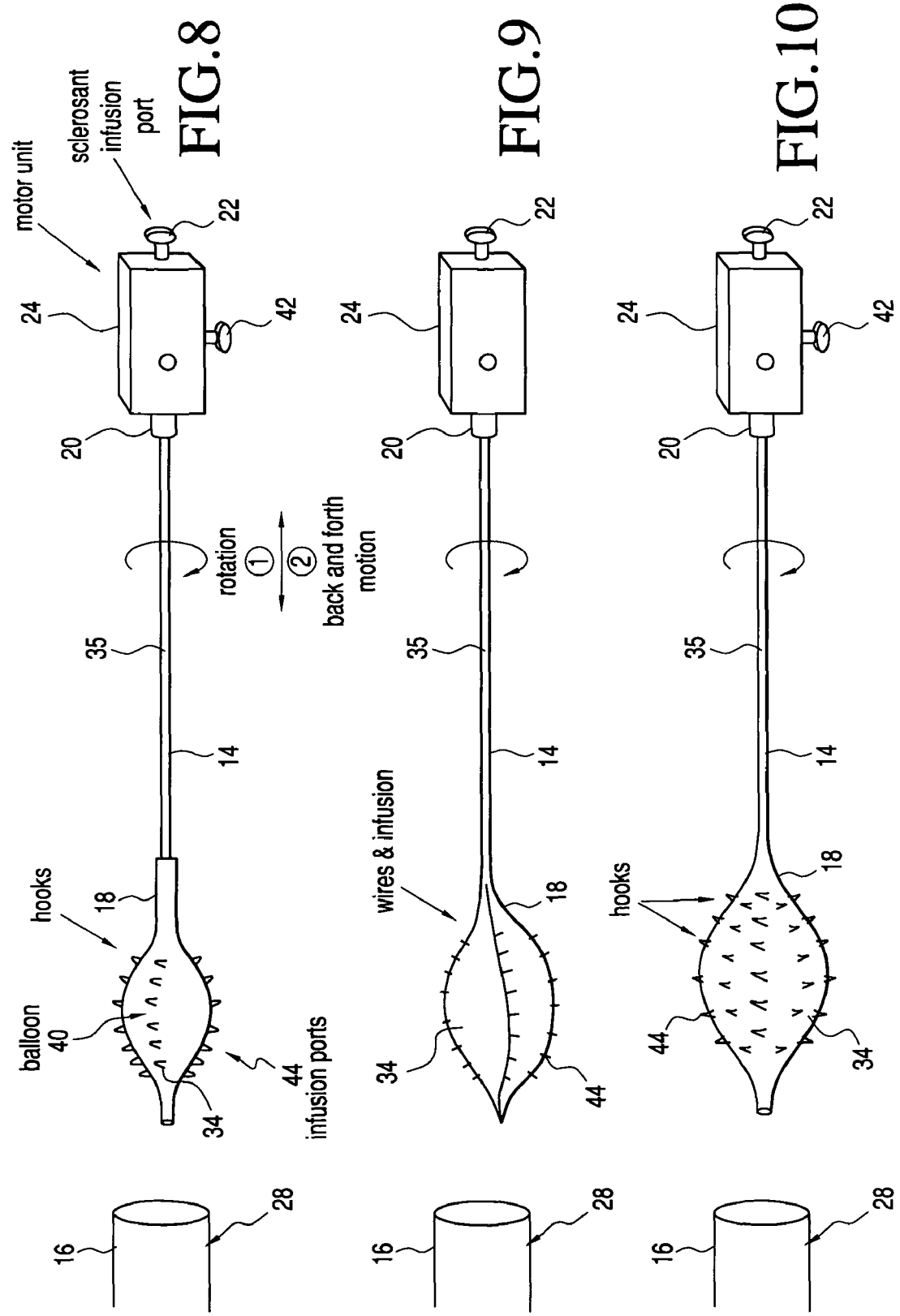

VASCULAR ABLATION APPARATUS AND METHOD

CROSS REFERENCE TO RELATED APPLICATIONS

This application is based upon U.S. Provisional Application Ser. No. 60/501,423, filed Sep. 10, 2003, entitled "VASCULAR ABLATION APPARATUS AND METHOD".

BACKGROUND OF THE INVENTION

1. Field of the Invention

The invention relates to a vascular ablation apparatus and method. More particularly, the invention relates to a vascular ablation apparatus that delivers a sclerosing solution during the disruption and/or irritation of a vessel wall. The invention further relates to a vascular ablation method wherein disruption and/or irritation of the vessel wall is combined with the application of sclerosant.

2. Description of the Prior Art

Venous stasis is a common condition in which the flow of blood from the legs to the heart is abnormal. Most people assume that the heart pumps blood out to the legs and then pumps it back. That's only half right. Actually, the heart only pumps the blood out. Leg muscles pump it back. Every time a leg muscle tightens (called contraction), it squeezes the leg veins flat. Blood is pushed through the veins like toothpaste being squeezed from a tube. When everything is working normally, a series of one-way gates (called valves) make sure the blood can only move one direction; that is, toward the heart. However, when the valves are damaged, the "muscle pump" doesn't work (imagine a busy intersection with no traffic signals). This condition is called reflux and most often involves a large leg vein called the saphenous vein. When saphenous reflux is present, blood simply pools in the legs, causing everything from unsightly varicose veins to severe pain and ulceration of the skin.

The treatment options for venous stasis are currently limited. The traditional therapy used to treat venous reflux in the saphenous vein is surgical stripping and ligation. This procedure is performed by surgeons and often involves general anesthesia in a hospital setting. Vein stripping and ligation begins with an incision in the groin region to expose the saphenous vein; once identified the surgeon "ligates" or ties off the saphenous vein and small veins with sutures. A second incision is made either just below the knee or at the ankle for the same purpose. Once both ends of the vein are free, a thin wire-like instrument called the stripping tool is threaded through the vein from the groin to the second incision. The stripping tool is tied to the vein and the vein is pulled out, or stripped, and removed from the leg. Some common side effects from vein stripping and ligation surgery may include temporary pain or discomfort, bruising, hematoma, numbness, and less frequently wound infection.

In addition to stripping, laser treatment is currently available. Endovenous laser treatment allows delivery of laser energy directly into the blood vessel lumen in order to produce endothelial and vein wall damage with subsequent fibrosis. It is presumed that destruction of the greater saphenous vein with a laser is a function of thermal destruction. The presumed target is intravascular red blood cell absorption of laser energy. However, thermal damage with resorbtion of the greater saphenous vein has also been seen in veins emptied of blood. Therefore, direct thermal effects on the vein wall probably occur. The extent of tissue thermal injury is strongly dependent on the amount and duration of heat exposure.

Radio-Frequency treatments are also used. For example, The VNUS Closure procedure (www.vnus.com) is a minimally invasive option for patients with superficial venous reflux and varicose veins. Using radiofrequency (RF) energy and a catheter based approach, the closure procedure occludes veins thereby eliminating reflux.

Potential complications of laser and RF include, but are not limited to the following: vessel perforation, thrombosis, pulmonary embolism, phebitis, hematoma, infection, paresthesia and skin burn. Treatment of veins located very close to the skin surface may result in a skin burn. Paresthesia may occur from thermal damage to adjacent sensory nerves. The risk of paresthesia is higher with treatment at or below the calf.

Vein sclerotherapy has been a treatment in Europe since the 1960's. It is an injection technique for treating various vein conditions such as; varicose veins, reticular veins, spider veins of the leg, and also some fine facial veins. Varicose and spider veins are predominant in women and affect about 40% of the population.

Sclerotherapy is the treatment of choice for the smaller spider or thread veins, which are so common on the face and legs. Sclerotherapy is a 30-minute, virtually painless procedure with huge advantages over surgery, including no general anesthetics, no stitches, no hospitalization and no time off work.

The mechanism of sclerotherapyis as follows. Vascular fibrosis and obliteration only occurs in response to irreversible endothelial cellular destruction and exposure of the underlying subendothelial cell layer. If an injected sclerosant is too weak, there may be no endothelial injury at all. If the sclerosant is a little stronger, the varicose vessel is damaged, but recanalization occurs and an incompetent pathway for retrograde blood flow persists. If the injected sclerosant is too strong, the varicose vessel endothelium is destroyed, but the sclerosant may flow into adjacent normal vessels and causes damage there as well. The key goal is to deliver a minimum volume and concentration of sclerosant that will cause irreversible damage to the endothelium of the abnormal vessel to be sclerosed, while leaving adjacent normal vessels untouched. It is important to protect normal superficial vessels, and it is critically important to avoid injuring the endothelium of deep veins, because deep vein thrombosis places patients at risk of death from thromboembolism, as well as causing permanent disability from chronic deep venous valvular insufficiency. The rational treatment of varicosities and telangiectasias by chemical sclerosis depends upon the ability to produce vascular endothelial damage that is irreversible in the area under treatment, but that does not extend to adjacent normal vessels.

Sclerosant is diluted with blood as it diffuses away from the site of injection. Thus, if a strong sclerosant is injected, there will be three zones of action. In zone 1, vascular endothelium is irreversibly injured; the vessel will be fully sclerosed and eventually will be completely replaced by a fibrous tissue. In zone 2, vascular endothelium is injured, and the vessel will be partially or completely thrombosed but will eventually recanalize. In zone 3, the sclerosant will be diluted below its injurious concentration, and there will be no endothelial injury.

Because dilution of the sclerosant with blood occurs immediately upon injection, the original injected concentration is of no real importance. What is important is the diluted concentration of sclerosant at the surface of the endothelium. An injected concentration that is perfectly effective in a spider vein (where sclerosant displaces blood rather than mixing with it) may be ineffective in a reticular feeding vein or a truncal varix simply because dilution reduces the final concentration so low that there will be no endothelial injury whatsoever. If the injected concentration is too high, dilution will leave the final concentration so high that endothelial damage will occur where it is not wanted. If the injected concentration is just right, dilution will leave a final concentration that is sufficient to injure the local varicose endothelium, but not high enough to damage normal superficial or deep veins. With big vessels, sclerotherapy alone is not sufficient to guarantee venous occlusion and destruction; success rate of sclerotherapy alone in permanently occluding the vein is about 60%, therefore enhancement of the sclerosis procedure is needed.

When one selects a particular volume and concentration of a chemical agent with which to sclerose a vessel, they explicitly or implicitly adjust the injected concentration and volume to take into account the dilution that will occur when the sclerosant is mixed with blood immediately after injection. One must also take into account the further dilution that will occur as the sclerosant flows or diffuses away from the site of injection.

Vascular spasm is usually and unwanted phenomena of vessels in general and veins in particular. Spasm of the greater saphenous vein can occur during a cardiac bypass surgery and after graft implantation. Arterial spasm can also occur and can result in an infarction. Vascular spasm also occurs with excessive manipulation of vessels with catheters or guide wires. Without any additional irritation venous spasm usually resolves spontaneously. Because of the cylindrical geometry of blood vessels, the volume contained in a vessel depends on the square of the vessel radius: the volume of any cylinder is calculated as $(pi)(r2)(L)$ (where r is the radius and L is the length of the vessel). During spasm the diameter of the vessel is reduced dramatically, up to 5 to 10 fold smaller, decreasing the volume of blood within the vein by a magnitude of 25 to 100.

In view of the shortcomings of prior treatment techniques and apparatuses, a need exists for an improved apparatus and method for treating venous stasis. The present invention provides such an apparatus and method.

SUMMARY OF THE INVENTION

It is, therefore, an object of the present invention to provide an apparatus for the treatment of venous stasis. The apparatus includes an elongated intraluminal member shaped and dimensioned for passage through vessels of a subject. The intraluminal member includes a proximal end and a distal end. A conduit extends from proximate the proximal end of the intraluminal member to proximate the distal end of the intraluminal member. The conduit is shaped and dimensioned for fluid communication between the proximal end of the intraluminal member and the distal end of the intraluminal member. The distal end of the intraluminal member includes disruption means proximate thereto for disrupting or irritating a predetermined vessel wall.

It is also an object of the present invention to provide an apparatus that irritates the vein for the purpose of creating vein spasm.

It is also an object of the present invention to provide an apparatus wherein the intraluminal member comprises an infusion wire.

It is another object of the present invention to provide an apparatus wherein the distal end of the intraluminal member is sinusoidal.

It is a further object of the present invention to provide an apparatus wherein at least one application port in fluid communication with the conduit is formed in the distal end of the intraluminal member, the at least one application port being positioned at an upper or lower extent of the sinusoidal infusion wire.

It is yet another object of the present invention to provide an apparatus wherein the distal end of the intraluminal member is substantially V-shaped.

It is still another object of the present invention to provide an apparatus wherein the distal end of the intraluminal member is substantially J-shaped distal.

It is also a further object of the present invention to provide an apparatus wherein the distal end of the intraluminal member is circular.

It is still a further object of the present invention to provide an apparatus wherein the intraluminal member includes a twisted circular distal end.

It is yet a further object of the present invention to provide an apparatus wherein the infusion wire is a shape memory material and the apparatus further includes a stiffener associated with the distal end of the intraluminal member.

It is also an object of the present invention to provide an apparatus wherein the intraluminal member is a balloon catheter.

It is another object of the present invention to provide an apparatus wherein a balloon is positioned at the distal end of the intraluminal member and the balloon includes at least one application port in fluid communication with the conduit.

It is a further an object of the present invention to provide an apparatus wherein the balloon includes a plurality of protrusions shaped and dimensioned for scraping or injuring the surface of the vessel wall.

It is also another object of the present invention to provide an apparatus wherein the intraluminal member includes a multi-prong assembly.

It is also a further object of the present invention to provide an apparatus wherein the intraluminal member includes a multi-infusion wire assembly.

It is also an object of the present invention to provide an apparatus including means for movement of the intraluminal member to facilitate disruption or irritation of the predetermined vessel wall.

It is another object of the present invention to provide a method for the treatment of venous stasis. The method is achieved by advancing an elongated intraluminal member through a vein to a treatment site, activating the intraluminal member for disruption or irritation of the treatment site and injecting sclerosant into the vein at the treatment site.

It is a further object of the present invention to provide a method wherein the step of activating includes moving the intraluminal member to cause disruption or irritation of the vessel.

It is also an object of the present invention to provide a method including the step of causing spasms within the vein.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 8, 9 and 10 are embodiments of the present invention wherein a balloon catheter is utilized.

DESCRIPTION OF THE PREFERRED EMBODIMENTS

Figure 1:
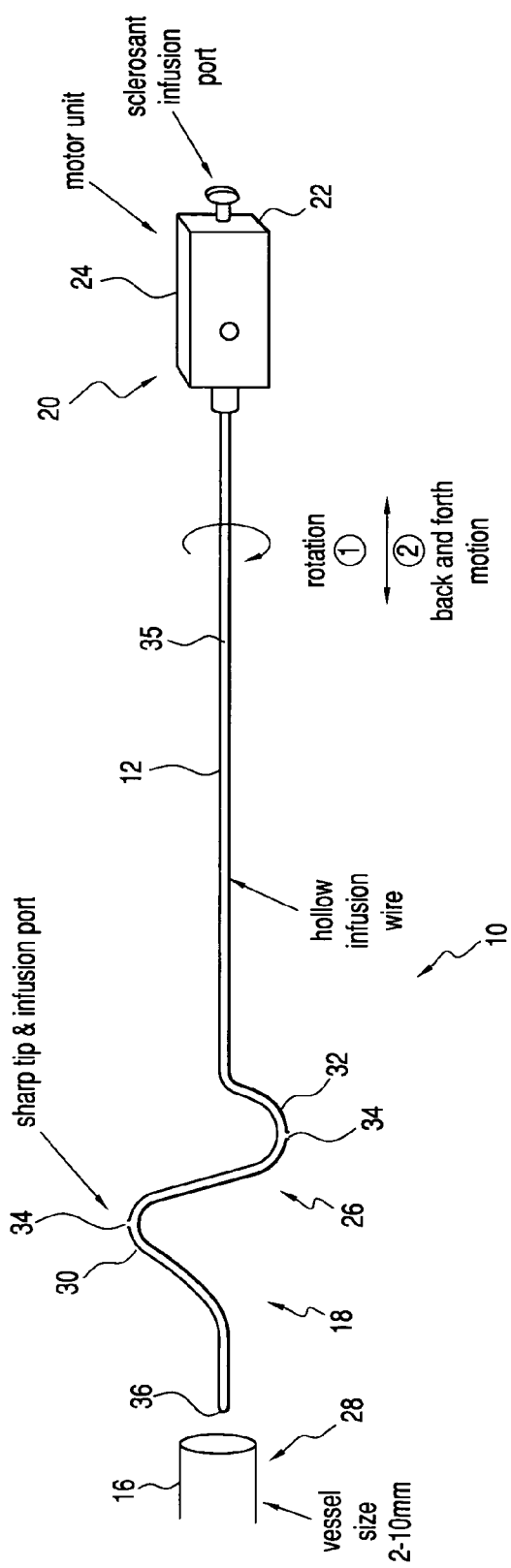
FIG. 1 is a schematic of an embodiment utilizing an infusion wire.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

With reference to the various embodiments disclosed in FIGS. 1 to 14, an apparatus 10 and method for the treatment of venous stasis, for example, varicose veins, is disclosed. Although the present apparatus 10 and method are described with reference to its use in treating varicose veins, the present apparatus and method may be employed in other applications without departing from the spirit of the present invention. In addition, various embodiments of the present apparatus are disclosed below and the same reference numerals are used in designating similar parts within these different embodiments.

In general, the apparatus 10 includes a wire 12 (see FIGS. 1, 2, 3, 4, 5, 6, 7a and 7b), balloon catheter 14 (see FIGS. 8, 9 and 10), multi-prong assembly 15 (see FIGS. 11 and 12) or multi-infusion wire assembly 60 (see FIG. 13) capable of delivering a sclerosant material while irritating and/or disrupting the vessel wall 16 of the treatment site. While the terms irritating and/or disrupting are utilized in describing the present invention, those skilled in the art will understand that these terms may be used substantially interchangeably without varying the scope of the present invention.

The present apparatus 10 treats varicose veins by disrupting and/or irritating a vessel wall 16 in conjunction with the direct administration of a sclerosant material. This direct delivery of the sclerosant to the irritated or disrupted vessel provides for improved success rates in the treatment of varicose veins when compared with the limited success rates for traditional sclerotherapy as discussed above with reference to prior art techniques. In addition to the enhanced effectiveness achieved through the combined implementation of disruption and/or irritation and sclerotherapy, the vein spasms produced as a result of the apparatus 10 will further enhance the efficacy of the procedure.

Further to the various embodiments described below, delivery of sclerosant can be done either before, during or after vascular irritation and/or disruption. The location and method of delivery of sclerosant can be done either at the sclerosing site, proximal to it, distal to it, as well as at the vascular entry site through a vascular sheath. In addition, and as those skilled in the art will certainly appreciate, it is contemplated the delivery of the sclerosant may be achieved at a variety of locations, including system administration. Although the invention is primarily directed to the use of mechanical disruption devices, it is contemplated that other disrupting mechanisms (for example, heat, cold, electrical, laser, Radiofrequency, etc.) may be employed within the spirit of the present invention.

As is discussed below in greater detail, the wire 12, balloon catheter 14, multi-prong assembly 15 or multi-infusion wire assembly 60 is moved to create the disruption and/or irritation in the vessel wall. In general, the disruption and/or irritation is caused by a mechanical device, which when positioned in the vessel provides an outwardly directed radial force to engage, irritate and damage but not break through the inner vessel wall.

As will be described below in greater detail, the mechanical device may take the form of a wire, catheter, balloon, spring, brush or a combination thereof. Movement may either be created by rotation of the apparatus 10, by linear movement of the apparatus 10 or by a combination of both rotational and linear movement of the apparatus 10. In addition, the movement may be achieved via either manual actuation or via the implementation of a power system.

With reference to FIG. 1, a first embodiment is disclosed. The apparatus 10 functions by disrupting and/or irritating the lining of the vessel wall 16 and delivering a sclerosing solution directly to the vessel wall 16 for safe and easy ablation. The apparatus 10 includes an infusion wire 12 having a distal end 18 and a proximal end 20. While the term "wire" is used in the present description it is contemplated that various materials (for example, metals, plastics, etc.) may be used without departing from the spirit of the present invention. For example, it is contemplated the infusion wire might take the general form of a catheter shaped and dimensioned to function in the manner detailed herein. In addition, the structure of the wire itself may be varied to suit specific needs; for example, the distal end of the wire may be solid or incorporate a spring structure to provide for desired rigidity. With the foregoing in mind, those skilled in the art will appreciate the wide variety of possible structures which may be employed without departing from the spirit of the present invention.

At its proximal end 20, the infusion wire includes a sclerosant infusion port 22 for supply of the sclerosing agent to the infusion wire 12. In addition, a motor 24 is coupled to the proximal end 20 for the controlled rotation of the infusion wire 12 in a manner which will be discussed below in greater detail.

The distal end 18 of the infusion wire 12 is provided with a series of sinusoidal waves 26 shaped and dimensioned for engaging the vessel wall 16 of the vessel 28 into which the infusion wire 12 is placed. At the upper and lower extents 30, 32 of the sinusoidal waves 26 of the infusion wire 12, the infusion wire 12 is provided with application ports 34 through which the sclerosing agent is administered within the vessel 28. The application ports 34 are in fluid communication with the infusion port 22 via a conduit 35 extending through the wire 12. By providing the application ports 34 adjacent the upper and lower extents 30, 32 of the infusion wire 12, sclerosing agent is applied almost directly to the vessel wall 16 being disrupted and/or initiated by the rotating infusing wire 12. Controlled administration of the sclerosing agent through the application ports 34 is enhanced by closing off the distal tip 36 of the infusion wire 12 so as to ensure the sclerosing material is administered only though the application ports 34 at the upper and lower extents 30, 32 of the infusion wire 12. Those skilled in the art will appreciate that proximal to the disrupting and/or irritating end the infusion wire may be enclosed in a sheath.

Figure 2:
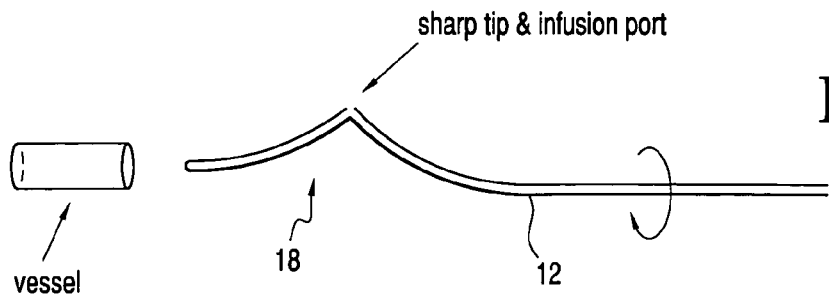
FIGS. 2, 3, 4, 5, 6, 7*a* and 7*b* are further embodiments of the present invention utilizing an infusion wire.
Figure 3:
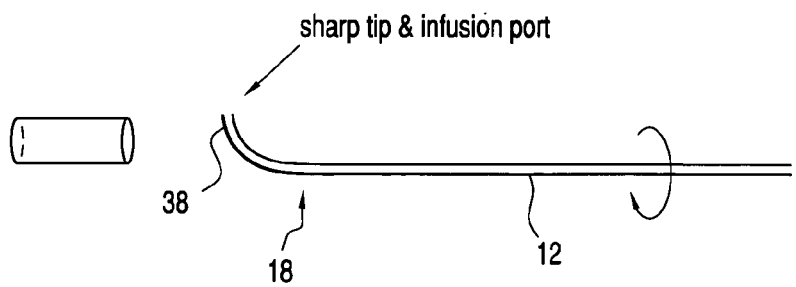
Figure 4:
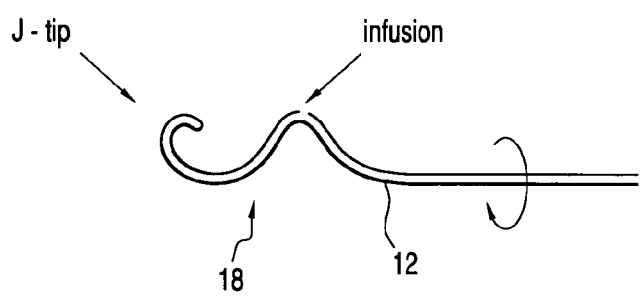
Figure 5:
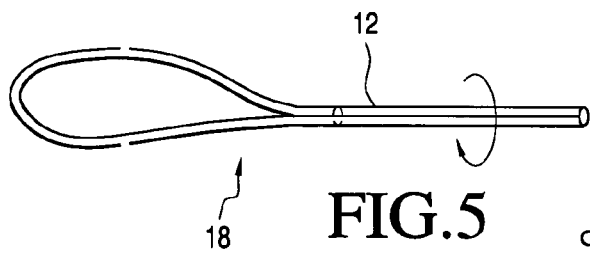
Figure 6:
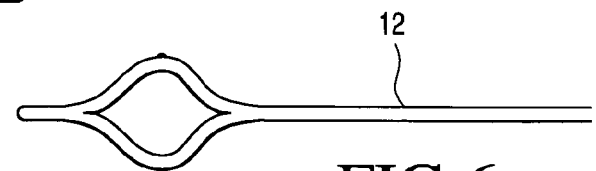

Further embodiments are disclosed with reference to FIGS. 2, 3, 4, 5 and 6. These embodiments are substantially similar to those disclosed above with reference to FIG. 1, however, the distal end 18 is shaped differently. For example, FIG. 2 provides an infusion wire 12 with a substantially V-shaped distal end 18, FIG. 3 provides an infusion wire 12 with a sharp tip 38 having an application port 34 therein, FIG. 4 provides an infusion wire 12 with a substantially J-shaped distal end 18, FIG. 5 provides an infusion wire 12 with a circular distal end 18 and FIG. 6 provides an infusion wire 12 with a twisted circular distal end 18. As those skilled in the art will most certainly appreciate, a wide variety of shapes may be employed without departing from the spirit of the present invention.

As those skilled in the art will certainly appreciate, it will be necessary to control the shape of the infusion wire 12 prior to insertion of the apparatus 10 within the vessel 28. It is contemplated this may be accomplished via the use of a stiffener which holds the infusion wire 12 in a desired configuration prior to insertion or through the fabrication of the infusion wire 12 from shape memory materials trained to assume the desired shaped when exposed to elevated temperatures within the body. This may also be accomplished by containment of the wire 12 in a sheath.

Figure 7A:
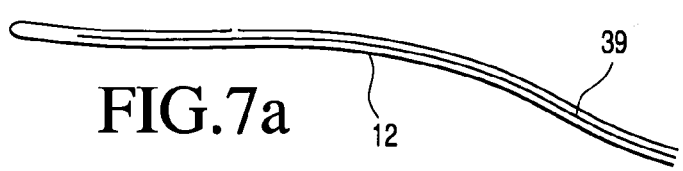
Figure 7B:
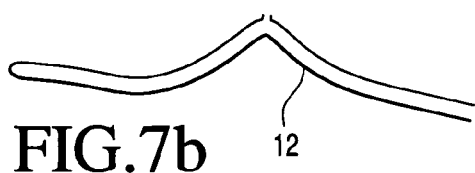

With reference to FIGS. 7a and 7b, an embodiment of the infusion wire 12 utilizing a stiffener 39 is shown. With reference to FIG. 7a, the stiffener 39 is positioned within the infusion wire 12. The stiffener 39 holds the infusion wire 12 in a straightened configuration allowing insertion through a needle or sheath (not shown). Once the infusion wire 12 is positioned at a desired location, the stiffener 39 is withdrawn and the infusion wire 12 resumes its desired configuration (see FIG. 7b) permitting disruption and/or irritation of the vessel wall 16 while a sclerosing agent is applied to the vessel wall 16.

Referring to FIGS. 8, 9 and 10, the infusion wire 12 may be replaced with a balloon catheter 14 shaped and dimensioned specifically for use in accordance with the present invention. More specifically, and as with the infusion wire 12, the balloon catheter 14 includes a proximal end 20 and a distal end 18 with the balloon 40 itself positioned adjacent the distal end 18 of the catheter 14.

At its proximal end 20, the catheter 14 includes a sclerosant infusion port 22 for administration of the sclerosing agent to the balloon catheter 14. The sclerosant may also be used in the inflation of the balloon 40 and will leach into the surrounding area via application ports 34 directly after inflation of the balloon 40 (see FIG. 9). The application ports 34 are in fluid communication with the infusion port 22 via a conduit 35 extending through the balloon catheter 14. In the event it is not desired to utilize the sclerosant as the inflating fluid, the catheter 14 is provided with a balloon port 42 at the proximal end 20 (see FIGS. 8 and 10). The balloon port 42 provides for the administration of fluid used in controlling inflation and deflation of the balloon 40 in a convention manner. Where a distinct fluid is used in the inflation of the balloon 40, the sclerosant infusion port 22 is directly linked with the application ports 34 for the injection of the sclerosant within the vessel 28. Although a conduit is provided in accordance with a preferred embodiment of the present invention, sclerosant delivery may also be accomplished by containment of the wire proximal to the balloon in a sheath and delivering the sclerosant fluid or foam through the annular space between the wire shaft and sheath to exit near the distal end of the sheath into the vein.

Manual manipulations maybe used or a motor 24 may be coupled to the proximal end 20 for the controlled rotation of the balloon catheter 14 in a manner that will be discussed below in greater detail.

The distal end 18 of the catheter 14 is provided with a balloon 40 having a series of sharp or rugged bumps or edges or hooks 44 shaped and dimensioned for scraping and injuring the surface or lining of the vessel wall 16. With this in mind, a series of application ports 34 are formed in the wall of the balloon 40 for the delivery of the sclerosing agent to the vessel wall 16. The application ports 34 are linked to the sclerosing agent supply port 22 at the proximal end 20 of the catheter 14. As those skilled in the art will certainly appreciate, a variety of balloon catheter lumen structures are known for the delivery of medicinal agents to the surface of the balloon and these known catheter lumen structures may be employed within the spirit of the present invention.

As those skilled in the art will also appreciate, a variety of balloon designs are possible within the spirit of the present invention. In addition, different configurations for the destructing sharp or rugged bumps or edges or hooks may be employed within the spirit of the present invention. Sclerosant delivery may also be accomplished by containment of the wire proximal to the balloon in a sheath and delivering the sclerosant fluid or foam through the annular space between the wire shaft and sheath to exit near the distal end of the sheath into the vein.

As briefly mentioned above, use of the present ablation apparatus 10 will produce spasms within the vessel 28 being treated. Vessels 28, and in particular veins, develop spasms upon irritation. Spasm is generally a non-desirable situation in vascular procedures and is commonly avoided. However, the apparatus 10 described in accordance with the present invention purposefully creates spasms at the treatment site. The creation of spasms in accordance with the present invention results in a decrease in vein size that markedly limits flow in the vein. This effect, together with the mechanical initiation and destruction of the vein, makes the vein very susceptible to the sclerosing agent and increases the likelihood for successful treatment.

In fact, it is known that sclerotherapy of smaller veins is more likely to be successful and that lower concentrations of sclerosant are necessary. The reason is primarily the reduced flow and reduced volume of blood in the smaller vein.

Spasm of the vein will reduce the size of larger veins to that of smaller veins and limit flow and volume. This will dramatically increase the likelihood of successful treatment when employed in accordance with the present invention. Success rates associated with prior art sclerotherapy techniques are limited. The bigger the vein, and the more flow and blood are present in the vein, the less likely the sclerosant will achieve complete destruction. In accordance with the present invention, the mechanical disruption in conjunction with sclerotherapy increases the success rate of the procedure. This is achieved by delivery of the sclerosant to the vessel, by causing spasm that limits the flow in the vessel and by mechanical destruction and disruption of the endothelium.

With regard to the creation of spasms, it is contemplated the spasm will be created within a blood vessel, either an artery or a vein. The spasm can be created by mechanical irritation or any other way, including, but not limited to, electrical, chemical, thermal treatment. The spasm is preferably created by disruption of the endothelial layer of a blood vessel, without perforation of the vessel wall. It is further contemplated that the creation of spasm within the vessel may be achieved for the purpose of increasing its susceptibility to subsequent injury, whether chemical or other.

In accordance with a preferred embodiment of the present invention, treatment is achieved in the following manner. Regardless of which of the various embodiments are employed, the apparatus 10 is first advanced through the vein 28 to the treatment area. The apparatus 10 is then activated for disruption and/or initiation of the treatment site. As discussed above, movement of the apparatus 10 to accomplish disruption and/or initiation may be achieved either manually or mechanically.

Either before, during or after the apparatus 10 is functioning to disrupt and/or irritate the treatment site, sclerosant is injected into the vein 28 at the treatment site. As with the movement of the apparatus 10, the sclerosant may be administered either manually (for example, a manually actuated syringe) or automatically (for example, a controlled pumping system linked to the apparatus 10). During the procedure, the apparatus may be pulled through the vein 28 toward the access site. Upon completion of ablation, the apparatus 10 is removed from the vein 28.

In accordance with the embodiment described with reference to FIG. 1, the sinusoidal distal end 18 of the infusion wire 12 is inserted to a desired site within the vessel 28. The motor 24 is then activated, rotating the sinusoidal infusion wire 12 in a manner which disrupts and irritates the vessel wall 16. At the same time, the sclerosing agent is pumped into the infusion wire 12 and is dispensed at the treatment site via the application ports 34 located at the upper and lower extents 30, 32 of the sinusoidal waves 26 of the infusion wire 12.

With reference to the embodiment disclosed in FIGS. 2, 3, 4, 5, 6, 7a and 7b these embodiments employ structures substantially similar to that disclosed in accordance with FIG. 1 and consequently function in substantially the same manner. In accordance with the embodiments disclosed in FIGS. 2, 3, 4, 5, 6, 7a and 7b, the infusion wire 12 is angled with a port or ports 34 that deliver a sclerosing agent directly to the vessel 16. Each of these designs also provide for a sharp edge or edges that initiate the vessel wall 16 at the same time. It is contemplated the wire 12 can be inserted through a needle or a small sheath. This will allow this venous ablation procedure to be done in an office setting, without sedation or incisions in the skin.

As discussed above with reference to FIGS. 8, 9 and 10, a balloon catheter 14 may also be employed in accordance with the spirit of the present invention. The balloon 40 is provided with sharp or rugged bumps or edges or hooks 44 that will scrape and injure the surface or lining of the vessel wall 16. This apparatus 10 will block flow in the vein and simultaneously deliver the sclerosant to the vessel wall 16. This injury will facilitate the destruction of the vein. The balloon 40 and the destructing edges 44 may have variable diameters and shapes, based on the size of the vessel being treated.

Once positioned at the predetermined treatment site within the vessel 28, the balloon 40, which is inserted in a deflated state, is inflated under the control of applied fluid, preferably but not necessarily the sclerosing solution. Whether the sclerosing solution is used in expanding the balloon or not, the sclerosing solution is injected into the balloon 40 or a chamber within the balloon (not shown) while the balloon 40 is in the vein 28 to be ablated. The balloon 40 will be pulled back with or without rotation within the vein 28. As mentioned above, this movement may be done by hand or with a mechanical device (for example, a motor 24) rapidly rotating the balloon catheter apparatus 10. Further, and as discussed above, a mechanical device may also control the rate and volume of delivery of the sclerosant. The sclerosing solution will leach out of the balloon 40 directly to the disrupted vein wall. The effect of the sclerosing solution will be enhanced by the disruption or initiation of the vessel wall 16.

It is further contemplated the balloon catheter may be modified with a wire or wires over the balloon. The wire can have sharp edges that will disrupt the vessel. The wire can rotate with or without the balloon.

Figure 11:
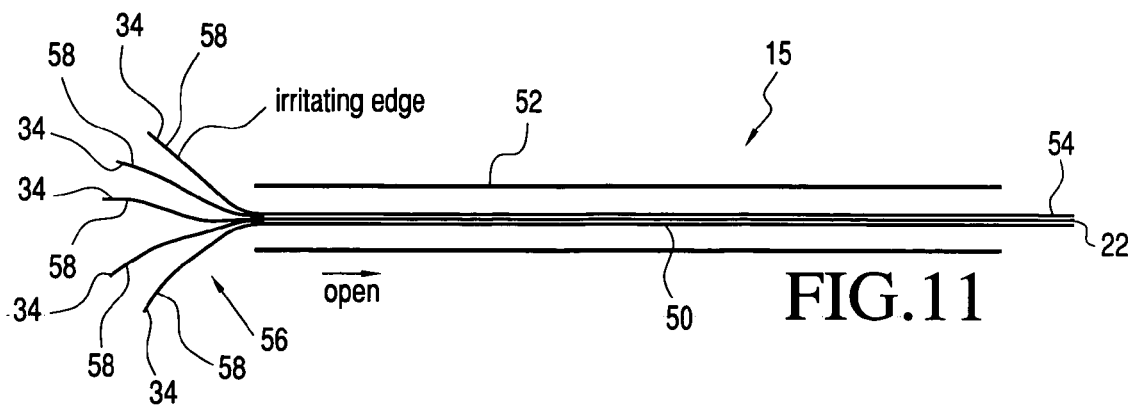
FIGS. 11 and 12 show still a further embodiment in accordance with the present invention.
Figure 12:
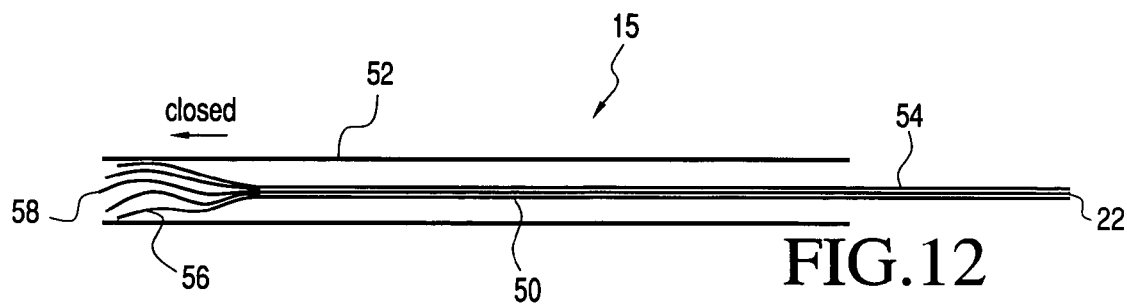

In accordance with yet a further embodiment of the present invention, and with reference to FIGS. 11 and 12, an ablation apparatus 10 is disclosed. The ablation apparatus 10 includes a multi-prong assembly 15 composed of a delivery member 50 housed within a sheath 52 adapted for movement relative to the delivery member 50. The delivery member 50 includes a proximal end 54 and a distal end 56. The proximal end 54 is a generally cylindrical member having an injection port 22 for the application of sclerosing agent toward the distal end 56 of the delivery member 50.

The distal end 56 of the delivery member 50 includes a series of outwardly biased prongs 58. The prongs 58 are biased such that when the sheath 52 is moved toward the proximal end 54 of the delivery member 50 and the prongs 58 are exposed (see FIG. 11), they extend outwardly into contact with the vessel wall 16. As such, the prongs 58 contact the vessel wall 16 permitting disruption and/or initiation of the vessel wall 16.

Sclerosing agent is delivered to the vessel wall 16 via ports 34 formed within the prongs 58. The ports 34 are formed so as to be in fluid communication with the injection port 22 located at the proximal end 54 of the delivery member 50.

In practice, the multi-prong assembly 15 is delivered to the treatment site in its storage configuration (see FIG. 12) with the sheath 52 covering the prongs 58. Once the multi-prong assembly 15 is delivered to the treatment site, the sheath 52 is moved relative to the delivery member 50 revealing the prongs 58 (see FIG. 11) and permitting the prongs 58 to extend outwardly into engagement with the vessel wall 16. Thereafter, the prongs 58 are moved to disrupt and/or irritate the vessel wall 16 either before, during or after a sclerosing agent is delivered.

As with the prior embodiments, the present ablation apparatus 10 may be either manually or automatically manipulated for both rotational and longitudinal movement during the disruption and/or initiation of the vessel wall 16.

Figure 13:
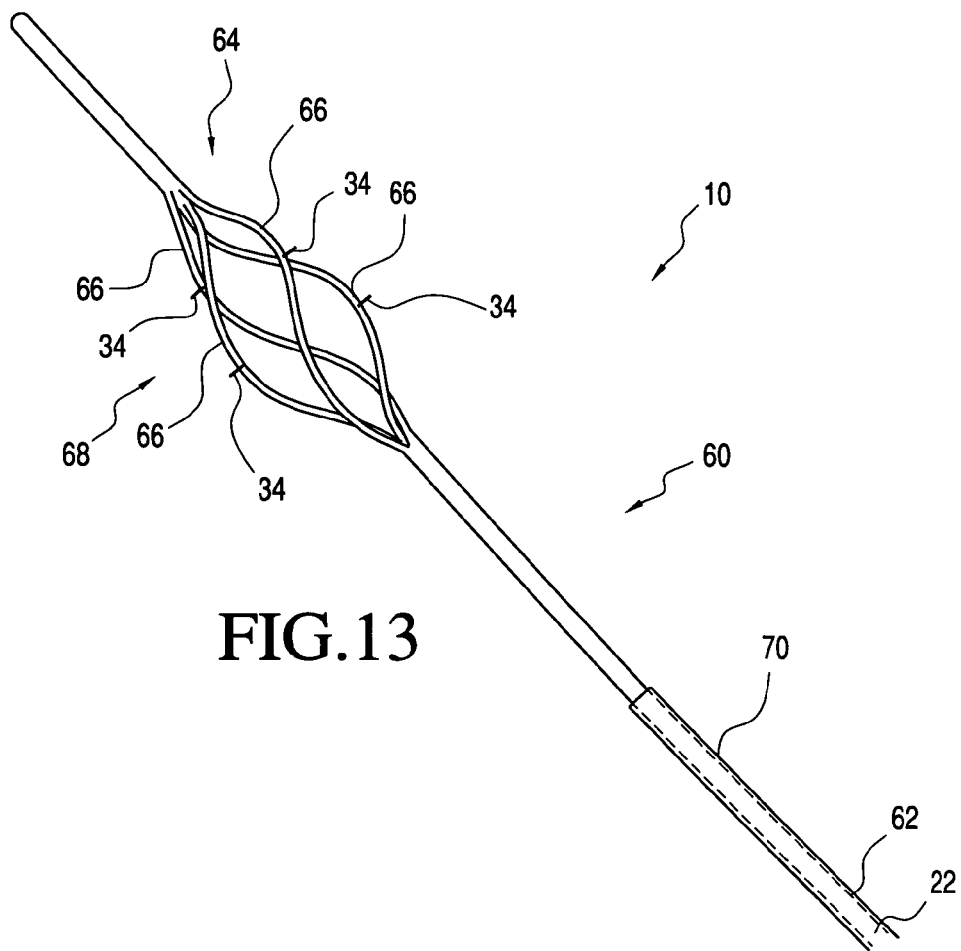
FIG. 13 is a perspective view of yet another embodiment in accordance with the present invention.

In accordance with still a further embodiment of the present invention, and with reference to FIG. 13, an ablation apparatus 10 is disclosed. The ablation apparatus 10 includes a multi-infusion wire assembly 60. The multi-infusion wire assembly 60 includes a proximal end 62 and a distal end 64. The proximal end 62 is a generally cylindrical member having an injection port 22 for the application of sclerosing agent toward the distal end 64 of the assembly 60.

The distal end 64 of the multi-infusion wire assemble 62 includes a series of helically wound wires 66 forming an elongated structure with an enlarged central region 68. The enlarged central region 68 is oriented outwardly such that the wires 66 may contact the vessel wall 16 for disruption and/or initiation in accordance with the present invention. Sclerosing agent is delivered to the vessel wall 16 via ports 34 formed within the wires 66. The ports 34 are formed so as to be in fluid communication with the injection port 22 located at the proximal end 62 of the assembly 60. In practice, the multi-infusion wire assembly 60 functions in much the same manner as the multi-prong assembly 15 disclosed with reference to FIGS. 11 and 12, and consequently includes a sheath 70 for delivery of the assembly 60. Sclerosant delivery may also be accomplished by delivering the sclerosant fluid or foam through the annular space between the wire shaft and sheath 70 to exit near the distal end of sheath 70 into the vein.

Figure 14A:
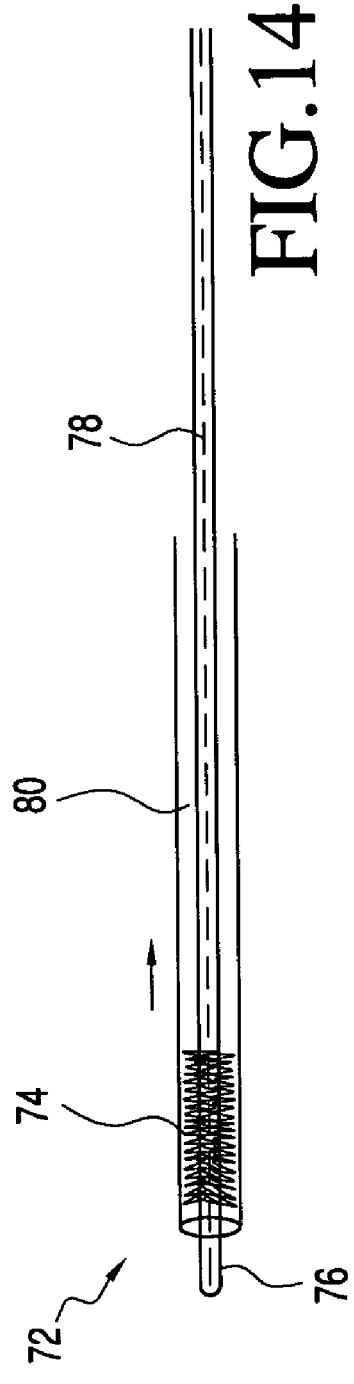
FIGS. 14a, 14b and 14c are schematics of yet another embodiment of the present invention.
Figure 14B:
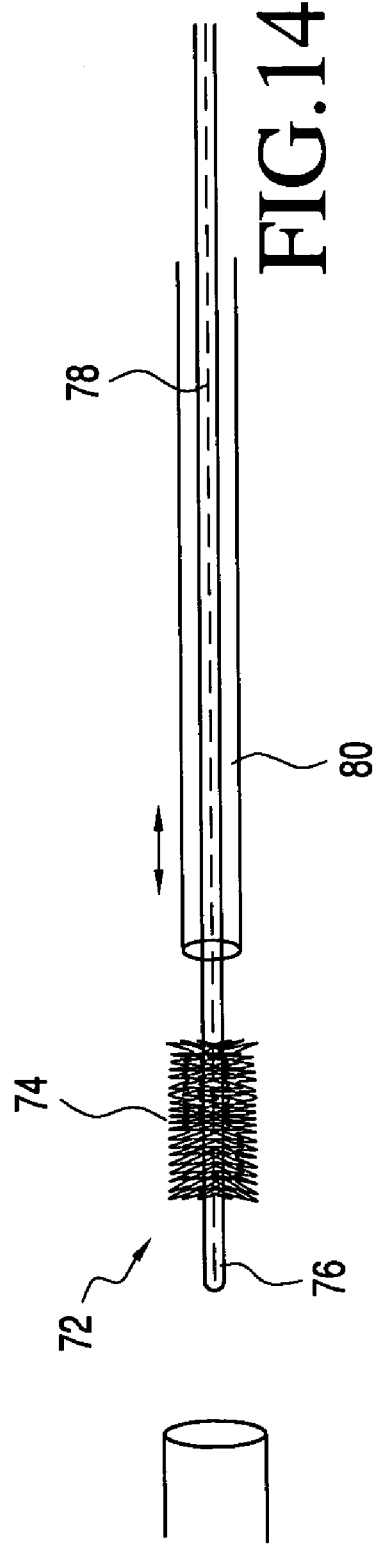
Figure 14C:
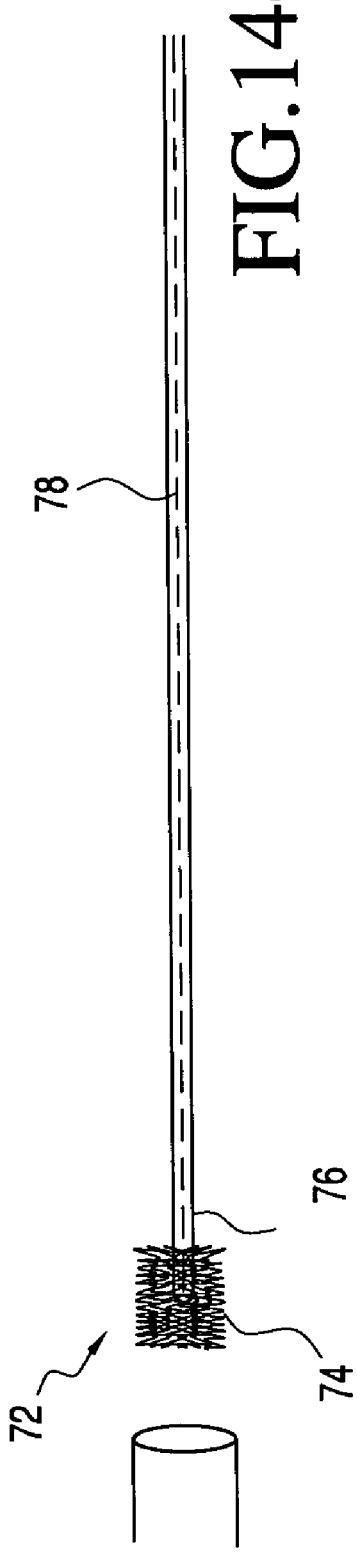

Yet a further embodiment of the present invention is disclosed with reference to FIGS. 14a, 14b and 14c. The ablation apparatus 72 is formed with a brush 74 at its distal end 76. The bush 74 may be positioned at the very end of the apparatus 72 (see FIG. 14c) or slightly removed from the end of the apparatus 72 (see FIGS. 14a and 14b). As with the other embodiments, the apparatus 72 includes a conduit 78 for the application of sclerosing agent to the treatment site. The apparatus 72 is further provided with a sheath 80 facilitating position of the apparatus 72 at a desired treatment site. The sheath 80 is utilized in a conventional manner to cover the distal end 76 of the apparatus 72 until it is properly positioned (see FIG. 14a), at which time it is withdrawn for treatment of the site (see FIG. 14b).

The brush 74 may be manually or automatically moved to created disruption at the treatment site. In accordance with an alternate embodiment, the sheath may function as a conduit providing a guiding tube for the application the sclerosing agent to the treatment.

In accordance with a preferred embodiment of the present invention, a variety of known sclerosing agents may be employed. Those skilled in the art will certainly appreciate the pros and cons of the known sclerosing agents and choose the sclerosing agent most appropriate for specific applications.

In addition to the delivery of liquid based sclerosing agents to a treatment site, it is further contemplated that foamed sclerotherapy may be employed in accordance with an alternate embodiment of the present invention. In order to deliver a high concentration of sclerosing agent into the vein wall, some researchers advocate the use of "foam sclerotherapy". This technique involves mixing the sclerosing solution with air or other gas, for example, oxygen, carbon dioxide and/or nitrogen to create foam. The idea behind this technique is to deliver a higher concentration of sclerosant to the vein wall.

More particularly, foam sclerotherapy employs a mixture of the sclerosant with gas creating microbubbles. The microbubbles displace the blood and ensure contact between the sclerosant and the vain wall. One potential disadvantage with the foam is that it can leach into the deep venous system and damage the endothelium there. This will cause deep venous thrombosis (DVT), a known complication of varicose vein treatment. DVT is less likely to occur when using liquid sclerosant. The liquid sclerosant gets diluted very quickly once it is flowing into the deep venous system and is therefore much less likely to cause endothelial damage and DVT.

As discussed above, the present invention is directed toward ablation of veins, especially the greater sephanous vein for treatment varicose veins. However, and as those skilled in the art will certainly appreciate, the present invention may be employed in the sclerosis and disruption and/or irritation of other hollow structures such as arteries, bronchi and any other organs, without departing from the spirit of the present invention.

The present invention further offers many cost advantages when compared with prior art techniques for the treatment of varicose veins. The currently available methods of large vein ablation include laser ablation, radio-frequency ablation and stripping. The present sclerotherapy wire method is less expensive as there is no need for a power generator.

With regard to safety concerns, prior art techniques are based on energy emission to "burn" the vein. The energy usually extends beyond the thin wall of the vein and can cause damage to the adjacent structures, including nerve damage and skin burns. It can also cause bleeding secondary to vascular disruption. The direct disruption-sclerotherapy method of the present invention, either with a wire or with a balloon catheter, will direct treatment to the vein wall and not beyond it.

Sclerotherapy has been used since the 1960's for ablation of veins. It is a safe and proven treatment. It is less effective in large veins because of the high flow and high volume causing rapid dilution of the sclerosant solution. The wire or balloon disruption delivery in accordance with the present invention ensures that the vein wall will be damaged and in contact with the appropriate concentration of sclerosant, regardless of the flow and blood volume in the vein.

Because of the risk of damage to adjacent tissue, before ablation with laser or RF, the operator needs to inject a large amount of local anesthetic, called tumescent anesthesia. This is very time consuming and might take up to 45 minutes depending upon the length of vein being treated. The present invention eliminates the need to use tumescent anesthesia.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for permanently occluding a vein through the combined disruption of a vein vessel wall and application of a sclerosant, comprising the following steps:
    advancing an elongated intraluminal member from an access site and into the vein, wherein the intraluminal member has a portion thereof configured to produce damage to an inner vessel wall of the vein under user control when performing a defined movement;
    damaging the inner vessel wall by performing the defined movement of the portion of the intraluminal member configured to produce damage against the vein's endothelium to disrupt the endothelium and ensure it is damaged and rendered susceptible to sclerosant; and
    injecting sclerosant into the vein and onto the damaged inner vessel wall;
    wherein the steps of damaging and injecting damages an extended portion of the inner vessel wall and exposes the extended portion to the sclerosant; and
    wherein the damage to the inner vessel wall comprises destruction and disruption of the endothelium sufficient to: (1) enhance the effect of the sclerosant, (2) facilitate the destruction of the vein, and (3) increase the likelihood of permanent vein occlusion from the injected sclerosant.

2. The method according to claim 1, wherein the step of moving comprises scraping the intraluminal member against the endothelium.

3. The method of claim 2, wherein the sclerosant is injected during scraping.

4. The method according to claim 1, wherein the intraluminal member comprises a hollow infusion wire, and the sclerosant is injected into the vein through the hollow infusion wire.

5. The method according to claim 1, wherein the elongated intraluminal member is a balloon catheter.

6. The method of claim 1, further comprising withdrawing the intraluminal member through the vein toward the access site while damaging the inner vessel wall and injecting sclerosant.

7. The method of claim 1, wherein the intraluminal member is advanced through a sheath, and the sclerosant is injected into the vein through an annular space between the intraluminal member and the sheath.

8. The method of claim 1, wherein the vein has a size of 2-10 mm.

9. The method of claim 1, wherein the defined movement comprises rotating the intraluminal member in the vein under the control of a motor so that a portion of the intraluminal member engages the endothelium.

10. The method of claim 9, wherein the portion of the intraluminal member that engages the endothelium is sharpened.

11. The method of claim 1, wherein the intraluminal member curves at a distal end.

12. The method of claim 1, wherein the intraluminal member is simultaneously rotated and moved longitudinally.

13. The method of claim 1, wherein the sclerosant is injected during the defined movement.

14. The method of claim 13, wherein the intraluminal member is rotated and moved longitudinally during scraping.

15. The method of claim 13, wherein the endothelium of the vein is disrupted without perforating the vein.

16. The method of claim 1, comprising moving the intraluminal member longitudinally.

* * * * *

UNITED STATES PATENT AND TRADEMARK OFFICE
CERTIFICATE OF CORRECTION

| | | |
|---|---|---|
| PATENT NO. | : 7,862,575 B2 | Page 1 of 1 |
| APPLICATION NO. | : 10/736535 | |
| DATED | : January 4, 2011 | |
| INVENTOR(S) | : Michael G. Tal | |

It is certified that error appears in the above-identified patent and that said Letters Patent is hereby corrected as shown below:

Title Page, Item (60), Related U.S. Application Data:

Should read as follows:

--Provisional application 60/501,423, filed on Sep. 10, 2003 and Provisional application 60/472,048, filed on May 21, 2003.--

Column 1, lines 5-7:

Should read as follows:

This application is based upon U.S. Provisional Applicalion Serial No. 60/501,423, filed September 10, 2003, entitled "VASCULAR ABLATION APPARATUS AND METHOD" and U.S. Provisional Application Serial No. 60/472,048, filed May 21, 2003, entitled "VASCULAR ABLATION DEVICE".

Signed and Sealed this
Fifteenth Day of February, 2011

David J. Kappos
*Director of the United States Patent and Trademark Office*